(12) United States Patent
Pisetta

(10) Patent No.: US 12,273,613 B2
(45) Date of Patent: Apr. 8, 2025

(54) OVER-THE-EYE APPARATUS FOR CAPTURING IMAGES FROM A USER'S POINT OF VIEW

(71) Applicant: Mariano Pisetta, Trento (IT)

(72) Inventor: Mariano Pisetta, Trento (IT)

( * ) Notice: Subject to any disclaimer, the term of this patent is extended or adjusted under 35 U.S.C. 154(b) by 237 days.

(21) Appl. No.: 17/753,859

(22) PCT Filed: Sep. 29, 2020

(86) PCT No.: PCT/IB2020/059085
§ 371 (c)(1),
(2) Date: Mar. 16, 2022

(87) PCT Pub. No.: WO2021/064562
PCT Pub. Date: Apr. 8, 2021

(65) Prior Publication Data
US 2022/0337729 A1  Oct. 20, 2022

(30) Foreign Application Priority Data
Sep. 30, 2019  (IT) .................. 102019000017465

(51) Int. Cl.
*H04N 23/58* (2023.01)
*G02B 27/01* (2006.01)
(Continued)

(52) U.S. Cl.
CPC ......... *H04N 23/58* (2023.01); *G02B 27/0172* (2013.01); *G02B 27/0179* (2013.01);
(Continued)

(58) Field of Classification Search
CPC ........ H04N 23/51; H04N 23/54; H04N 23/56; H04N 23/58; H04N 23/695; G02B 27/0172; G02B 27/0179; G06F 3/013
See application file for complete search history.

(56) References Cited

U.S. PATENT DOCUMENTS 10,511,731 B1 * 12/2019 Rao .................... G06F 3/005
11,163,166 B1 * 11/2021 Ebert ................ G02B 27/0176
(Continued)

FOREIGN PATENT DOCUMENTS

DE  102009002677 A1  10/2010

OTHER PUBLICATIONS

Schneider et al., "Movies Made Through the Eyes of a Mobile User With a Gaze-Aligned Camera", ICME, 2006, pp. 2121-2124.
(Continued)

*Primary Examiner* — Jeremiah C Hallenbeck-Huber
(74) *Attorney, Agent, or Firm* — LUCAS & MERCANTI, LLP

(57) ABSTRACT

An over-glasses apparatus, configured to be associated with a pair of glasses worn by a user, is disclosed. The apparatus includes a support structure, an eye tracking system, an image sensor, an actuation system of the image sensor, a camera housing, and means for processing and control. Advantageously, the image sensor and the actuation system of the image sensor are within the camera housing, arranged substantially in correspondence with a longitudinally median part of the main body, so that the camera housing intercepts an axis that connects the user's pupils.

16 Claims, 7 Drawing Sheets

(51) Int. Cl.
*G06F 3/01* (2006.01)
*H04N 23/51* (2023.01)
*H04N 23/54* (2023.01)
*H04N 23/56* (2023.01)
*H04N 23/695* (2023.01)

(52) U.S. Cl.
CPC .............. *G06F 3/013* (2013.01); *H04N 23/51* (2023.01); *H04N 23/54* (2023.01); *H04N 23/56* (2023.01); *H04N 23/695* (2023.01); *G02B 2027/0138* (2013.01); *G02B 2027/014* (2013.01); *G02B 2027/0178* (2013.01); *G02B 2027/0187* (2013.01); *G06F 3/012* (2013.01)

(56) References Cited

U.S. PATENT DOCUMENTS

| | | | | |
|---|---|---|---|---|
| 2009/0207239 | A1* | 8/2009 | Warmerdam | H02K 41/031 |
| | | | | 348/61 |
| 2013/0258270 | A1* | 10/2013 | Cazalet | G02C 5/008 |
| | | | | 351/158 |
| 2014/0375771 | A1* | 12/2014 | Gabara | H04N 23/661 |
| | | | | 348/46 |
| 2015/0244910 | A1* | 8/2015 | Marston | H04N 23/00 |
| | | | | 348/294 |
| 2016/0139265 | A1* | 5/2016 | Yahav | G02B 27/0093 |
| | | | | 356/614 |
| 2017/0330042 | A1* | 11/2017 | Vaziri | G02B 26/0875 |
| 2018/0249048 | A1* | 8/2018 | Fiebelkorn | H04N 21/234 |
| 2018/0275755 | A1* | 9/2018 | Massonneau | G06F 3/013 |
| 2019/0265476 | A1* | 8/2019 | Blum | G02B 3/0056 |
| 2020/0058196 | A1* | 2/2020 | Nelson | G07F 17/3204 |
| 2020/0197098 | A1* | 6/2020 | Chopra | A61B 90/39 |
| 2020/0349800 | A1* | 11/2020 | Ciardi | G06Q 30/0209 |
| 2023/0194899 | A1* | 6/2023 | Su | G02C 5/14 |
| | | | | 351/111 |

OTHER PUBLICATIONS

Kang et al., "Analysis of Electric Machine Charateristics for Robot Eyes Using Analytical Electromagnetic Field Computation Method", IEEE, 2014, vol. 50, No. 2, pp. 785-788.

International Search Report and Written Opinion for Corresponding International Application No. PCT/IB2020/059085, Apr. 1, 2021, 18 pages.

\* cited by examiner

OVER-THE-EYE APPARATUS FOR CAPTURING IMAGES FROM A USER'S POINT OF VIEW

CROSS-REFERENCE TO RELATED APPLICATIONS

This application is a 371 of PCT/IB2020/059085, filed Sep. 29, 2020 which claims the benefit of Italian Patent Application No. 102019000017465, filed Sep. 30, 2019.

TECHNICAL FIELD OF THE INVENTION

The present invention refers, in general, to devices of the so-called "smartglasses" type (intelligent glasses), capable of taking or capturing images and supplying them to a remote device.

BACKGROUND

It is common today for smartglasses to have a fixed webcam. Usually, this is positioned on the temporal sides of the device, often in correspondence with the temples, or, if positioned more centrally, at the height of the forehead.

However, making use of these tools (for example as a teaching aid to an operator), it was found that often the wearer of the eyeglass device, instead of moving the head to point the object of attention, would prefer to simply change the gaze of the eyes, keeping the position of the head unchanged. For those who are observing, for example via webcam, this generates an annoying image framing defect. Indeed, in some sessions in the operating room for the remote transmission of a spinal surgery, the surgeon while he was filming the operation with a smartglasses device, for transmission to remote students, instead of pointing to the operating table, frequently kept his head turned towards the assisting nurse, while his eyes looked down on the intervention area. Those who remotely observed clearly could not appreciate the whole procedure.

Furthermore, even by actively paying attention to the aiming of the camera, it was noticed that, in sessions with students who wore smartglasses (such as Google Glass®), followed by teachers in remote connection, the latter often urged students to turn their heads to better film the environment where they were operating. On the other hand, the students complained about the uncomfortable position in which they were forced to hold their heads, also lamenting joint pains in the neck and the unnatural position in which they had to keep their eyes.

In addition to this, the positioning of the fixed lateral camera, or on the forehead, in particular for close-up shots, causes distortions of the images captured compared to the actual image composed by the brain of a user starting from both images provided by the eyes.

The scientific publication Schneider E. et al: "Movies Made Through the Eyes of a Mobile User with a Gaze-aligned Camera" describes an eyewear type device that can be worn by a user comprising a system for tracking the movement of the user's pupils and a camera mounted centrally, in correspondence, also in this case, with the user's forehead, moved so as to follow the user's gaze. The camera is moved around three mutually perpendicular rotation axes by three rotary motors connected to the camera by means of transmission shafts and gears that operate independently of each other. As noted before, the camera positioned on the user's forehead produces an undesirable shift of the camera's point of view with respect to that of the observer. In addition to this, the camera handling system is very complex and bulky, with adverse consequences on the weight, practicality and cost of the device. Furthermore, the device does not easily adapt to a user who wants to use it in conjunction with normal eyeglasses.

SUMMARY OF THE INVENTION

The technical problem posed and solved by the present invention is that of providing an apparatus of the smart-glasses type, equipped with a camera or equivalent means capable of filming the object of a user's gaze, wherein the images are faithful to what the user actually sees.

Such problem is solved by an over-glasses apparatus or assembly according to claim 1.

Preferred features of the present invention are the subject of the dependent claims.

The invention provides for the arrangement of a camera housing at the height of the pupils of a user and in a central position between them. This allows the over-glasses apparatus to provide an image that is truly faithful to the one actually seen by a user.

The proposed over-glasses apparatus may comprise means for adjusting the position of the camera housing on a main body of the apparatus itself with respect to a Y axis, the latter corresponding to the trace of the sagittal plane of the user's body, i.e. to a generally vertical axis in an upright posture. In this way, the over-glasses apparatus can be easily adapted to many types of frames and face shapes of various users, while maintaining the advantages of positioning the camera at the height of the user's pupils.

In a preferred embodiment described and claimed below, the apparatus provides an actuation system of an image sensor that allows the camera housing to have small dimensions and a limited weight. These features further contribute to obtaining an over-glasses system in which the camera housing is at the height of the user's pupils.

Thanks to the presence of a specifically made support structure, the over-glasses apparatus adapts easily and stably to various types of glasses without providing significant additional bulk. The aforementioned technical characteristic is particularly relevant considering the number of people who use eyeglasses.

The use of this type of apparatus and this project can advantageously have countless applications, as it can be adapted to different situations; to illustrate the operability, some practical examples are provided below.

- Red Cross: useful for the necessary support for emergencies in remote sites, where the medical staff of ambulances or helicopters need an urgent consultation with a specialist who can see a critical situation in a targeted manner.
- Specialized and/or professional training institutes: for example in the University of Surgery, Dentistry, etc., in general where it is important to learn with precision systems.
- Construction and Engineering: for the detection and control of engineering structures, constructions (eg. checking the progress of a project by those who control remotely).
- Energy, airports and aviation: an oil platform in alarm that requires a specialist to give advice on the sequence of operations to be carried out; or in aeronautics the control and verification of aircraft before take-off, etc.
- Surgery and dentistry: Tutor of new procedural systems or technical equipment.

Defense and Security: night watchmen/security supervisors can contact or be contacted for surveys.

Disasters: civil protection, security, research.

Registration of Activities and Interventions: inspections, maintenance, medical interventions.

Other advantages, characteristics and methods of use of the present invention will become apparent from the following detailed description of some embodiments, presented by way of non-limiting examples.

BRIEF DESCRIPTION OF THE FIGURES

Reference will be made to the figures of the attached drawings, in which.

Figure 1:
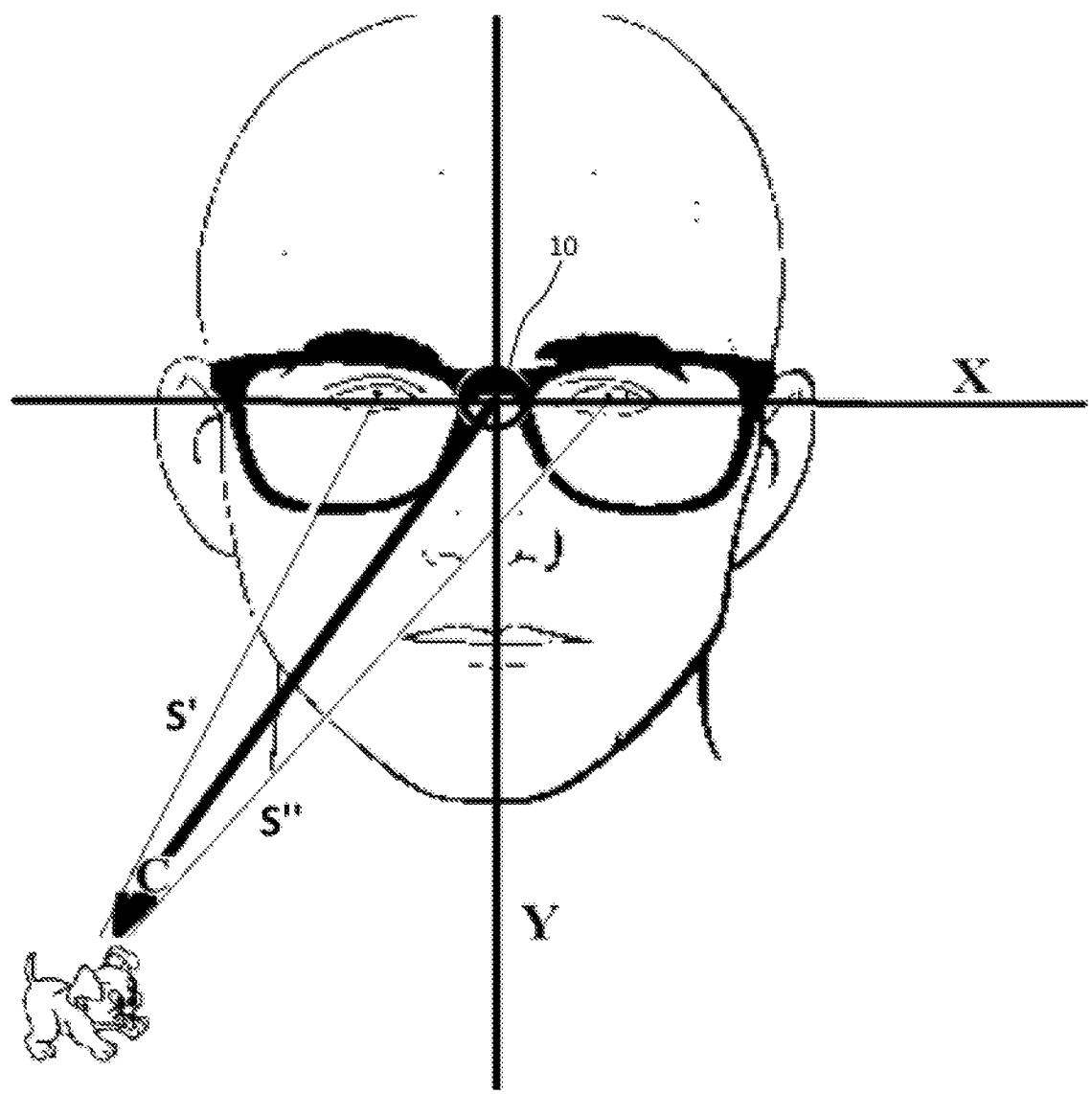
FIG. 1 shows a schematic view of a camera housing 10 (in the absence of a support structure 12), Cartesian axes X and Y, the collimation axis C and the face of a user wearing glasses.

The dimensions represented in the figures introduced above are intended as purely illustrative and are not necessarily shown in proportion.

DETAILED DESCRIPTION OF PREFERRED EMBODIMENTS

With reference to FIGS. 1, 3 and 6-8, an over-glasses apparatus according to an embodiment of the invention, configured to be associated with a pair of glasses worn by a user, mainly comprises:

a support structure 12;
an eye tracking system 18;
an image sensor 2;
an actuation system of the image sensor 2;
a camera housing 10; and
processing and control means.

All the other components introduced above are mounted on the support structure.

The supporting structure 12 has a main body 120 which has a longitudinal direction of prevailing development. This longitudinal direction of prevailing development defines an axis of the main body X'. The support structure 12 is configured to be positioned, when the over-glasses apparatus is associated with the user's glasses, above the lenses according to an arrangement in which the longitudinal direction of prevailing development is substantially parallel to the frontal anatomical plane. In other words, the longitudinal arrangement is perpendicular to the rods of the glasses and substantially parallel to the arrangement of the lenses.

The eye tracking system 18 is configured to detect, or record, the movement of at least one of the user's pupils.

The image sensor 2 is for example of the known type like NanEyeXS, weighing only 2 grams, equipped with an autofocus system.

The actuation system of the image sensor 2 is configured to allow rotation of the image sensor 2 at least around a first X axis and a second Y axis of a Cartesian axis system X, Y, Z, in which, in use, the first X axis is substantially an axis that connects the user's pupils (inter-pupillary axis), lying on the frontal plane of the user, the second Y axis is substantially an axis perpendicular to the X axis and lying in the sagittal plane, and the Z axis is an axis perpendicular to the X axis and the Y axis at the meeting point between the X axis and the Y axis and substantially parallel to the transverse or cranio-caudal plane. Consequently, when the over-glasses apparatus is associated with the user's glasses, the main body axis X is substantially parallel to the X axis.

Advantageously, the image sensor 2 and the actuation system of the image sensor 2 are comprised within a camera housing 10 arranged substantially in correspondence with a longitudinally median portion of the main body 120, so that the camera housing 10 intercepts the X axis. In other words, when the over-glasses apparatus is in use, the image sensor 2 is at the same level as the user's pupils. In this way, the images captured by the image sensor 2 correspond faithfully to what is actually seen by the user, as if sensor 2 were a "third eye".

The processing and control means are programmed to receive in input a detection signal supplied by the eye tracking system 18 and to control said actuation system according to respective angles of rotation of the image sensor 2 around the axis X and to the Y axis, so that the image sensor is continuously oriented according to the user's gaze. In other words, with reference to FIG. 1, the processing and control means are programmed to control the actuation system of the image sensor 2 so that this sensor 2 is oriented according to an axis of collimation C, passing through the position of the sensor 2 and a point of intersection of two axes S' and S", representative of the spatial orientation of each pupil of the user.

The eye tracking that determines the instantaneous orientation of the pupils can be performed according to methods and algorithms known in the art.

According to an embodiment, the over-glasses apparatus comprises means for adjusting the position with respect to the Y axis of the camera housing 10 with respect to the main body 120 of the support structure. In this way, the over-glasses apparatus can be adapted, in an even more advantageous way, to various types of glasses or users' face conformations, always ensuring that the camera housing 10 is at the same level as the user's pupils. The means for adjusting the position with respect to the Y axis are, for example, of the gear type, in particular comprising a worm screw connecting the camera housing 10 and the main body 120.

Figure 3:
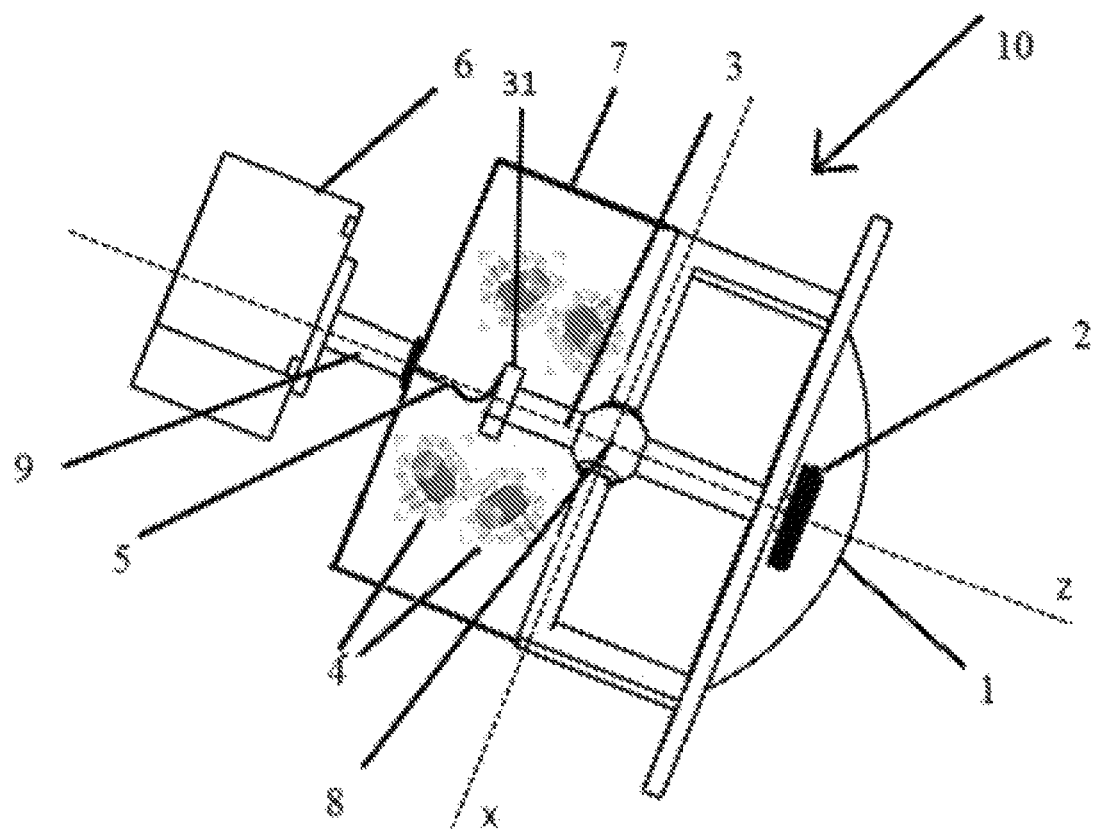
FIG. 3 shows a schematic representation of the actuation system of an image sensor 2.

According to an embodiment—and with reference to FIG. 3—the actuation system of the image sensor 2 comprises a shaft 3. The image sensor 2 is connected to a first end of such shaft 3. A body 31 in ferromagnetic material is connected to a second end of the shaft 3, opposite the first end.

This shaft 3 is constrained to the camera housing 10, with respect to the translation movement, at an intermediate point between the first and second ends by means of a structural constraint 8.

Furthermore, this structural constraint 8 is configured to allow the rotation of the shaft 3, initially directed according to the Z axis when it is in an initial rest position, around the X axis and the Y axis.

In other words, when the over-glasses apparatus is associated with a pair of glasses worn by a user, the structural constraint 8 is substantially located at the origin of the axes of the Cartesian system X, Y, Z. The transverse movement of the intermediate point of the shaft 3 is prevented by the structural constraint 8, while the rotation of each end of the shaft 3 is allowed around the X axis and the Y axis.

Continuing, the actuation system of the image sensor 2 comprises at least four inductors 4 rigidly connected inside said camera housing 10, arranged and configured to generate a magnetic attraction/repulsion force on the body 31.

The four inductors 4 are preferably arranged along a circumferential path, at regular intervals, in a plane parallel to an XY plane defined by the X and Y axes of the Cartesian X, Y, Z axis system. Furthermore, the positioning of the inductors is such that the body 31 is substantially placed at the centre of the circumferential path when the shaft 3 is directed according to the Z axis.

The inductors 4 are configured to be controlled by a control signal emitted at the output by the processing and control means so that the electromagnetic fields generated have an attraction or repulsion effect on the body 31 with a consequent rotational movement around the X axis and to the Y axis of the image sensor 2.

Figure 2:
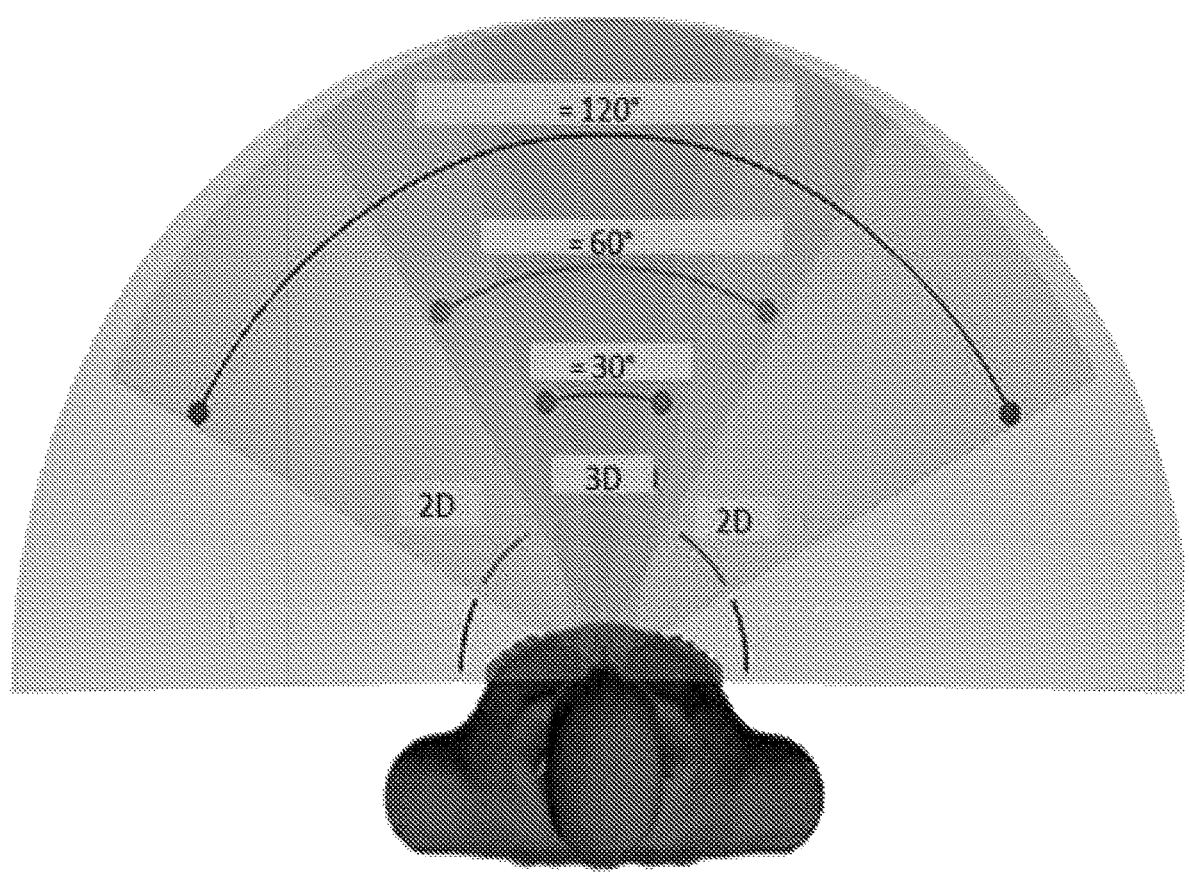
FIG. 2 shows a diagram depicting the width of the visual fields of each eye of an average human being.

Referring to FIG. 2, it can be observed that the gaze of an average human being has an overall radius of 120°, including the width of the peripheral visual field. According to one aspect, the rotation of the shaft 3 around the X axis and the Y axis is preferably comprised between an interval of ±80° and ±60° with respect to the initial position of the shaft 3, directed along the Z axis. Even more preferably, the rotation is substantially ±70°.

According to an embodiment, the actuation system of the image sensor 2 comprises springback means 5, a first end of which is connected to the body 31 and a second end of which, opposite the first, is connected to the camera housing 10. The springback means 5 are configured to be in a rest position when the shaft 3 is directed along the Z axis and to exert an elastic return force when the element 31 is attracted to one or more of the inductors 4. This elastic return force is suitable for bringing the shaft 3 back in the direction of the Z axis. The use of springback means 5 has the advantage of improving the fluidity of the movement of the shaft 3 and therefore of the image sensor 2.

Preferably, the camera housing comprises an optical unit configured to be placed in front of the image sensor 2. The optical unit, for example, can perform a magnification action or increase the field of view of the image sensor 2. In FIG. 3 the unit optical 2 is represented by a lens 1 placed in correspondence with a front portion of the camera housing 10 closed by side walls 7. It is to be understood that the lens 1 can also be simply transparent and have no optical effect on the image sensor 2.

According to an embodiment, the walls 7 are coated with a metal sheet for electromagnetic insulation, in order to prevent external magnetic forces from interfering with the movement of the body 31 inside the camera housing 10.

According to a variant embodiment, the over-glasses apparatus comprises an actuator 6, for example a micro stepper motor 6 with a threaded shaft 9, configured to move the camera housing 10 linearly along the Z axis. The actuator 6 is configured to operate when the visual field of the image sensor 2 is obstructed, at least partially, by the user's nasal septum. The processing and control means are, for example, configured to recognize this occurrence and appropriately activate the actuator 6 so that the camera housing moves away from the face of the user.

Figure 4:
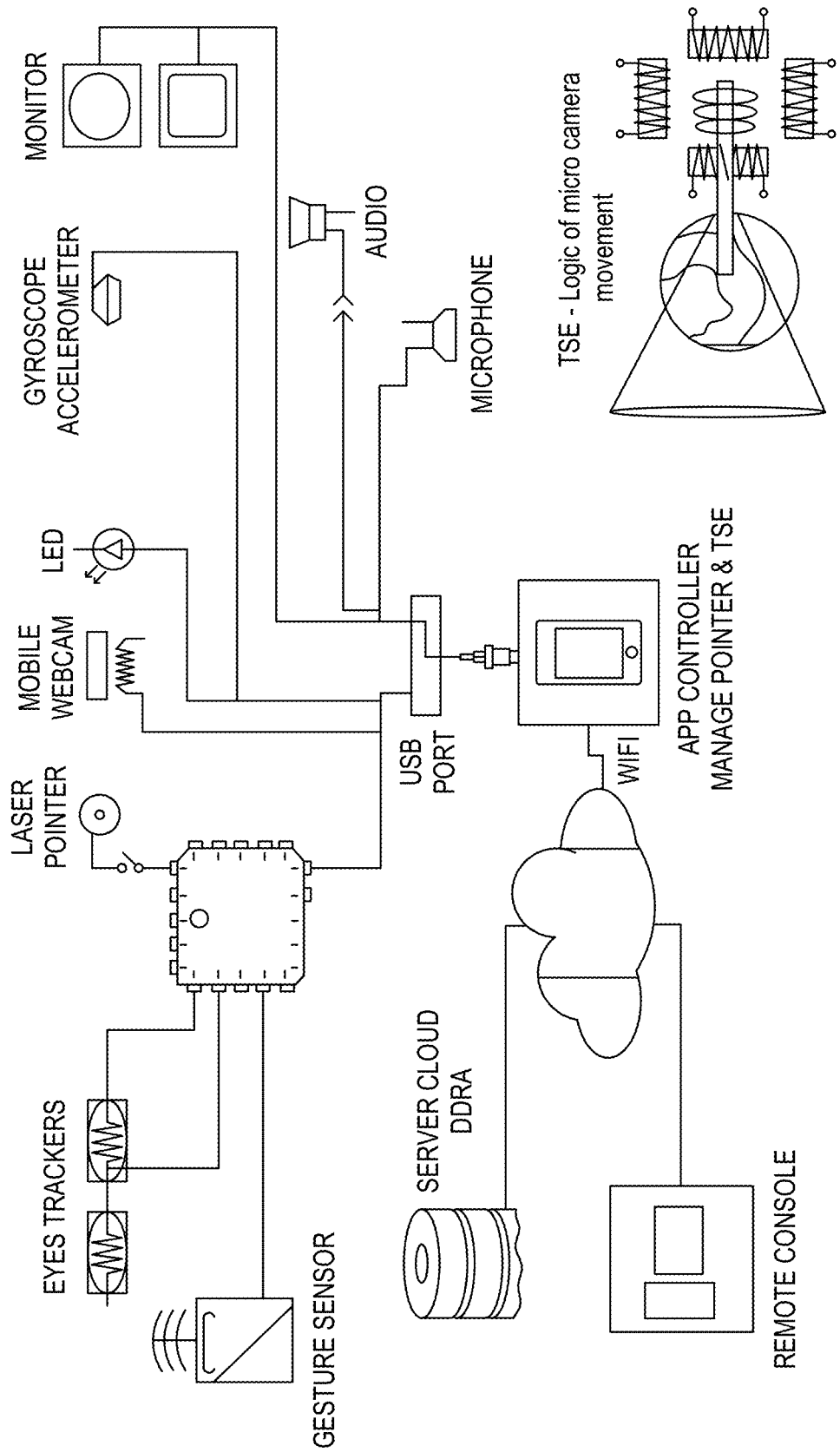
FIG. 4 shows a diagram of the components that make up an embodiment of the over-glasses apparatus.

Advantageously, with reference to FIG. 4, the over-glasses apparatus comprises an accelerometer and a gyroscope 22. These devices can be advantageously connected to an external camera (not worn by the user). The position and orientation of the user's face, combined with the information on the orientation of the pupils, allow the external camera, appropriately positioned, to also capture the object of the user's gaze. In this way, the public who watches the images captured by the image sensor 2 can also enjoy images captured from a second point of view.

According to one embodiment, the over-glasses apparatus comprises a semi-transparent monitor 19 configured to be positioned in front of one of the eyeglass lenses and to display information visible in transparency to the user of the over-glasses apparatus. Advantageously, the monitor 19 is configured to be moved from a position in which it is in front of the eyeglass lens to a position in which it is no longer visible by the user. The material used for the semi-transparent screen 19 is for example T-OLED.

Figure 5:
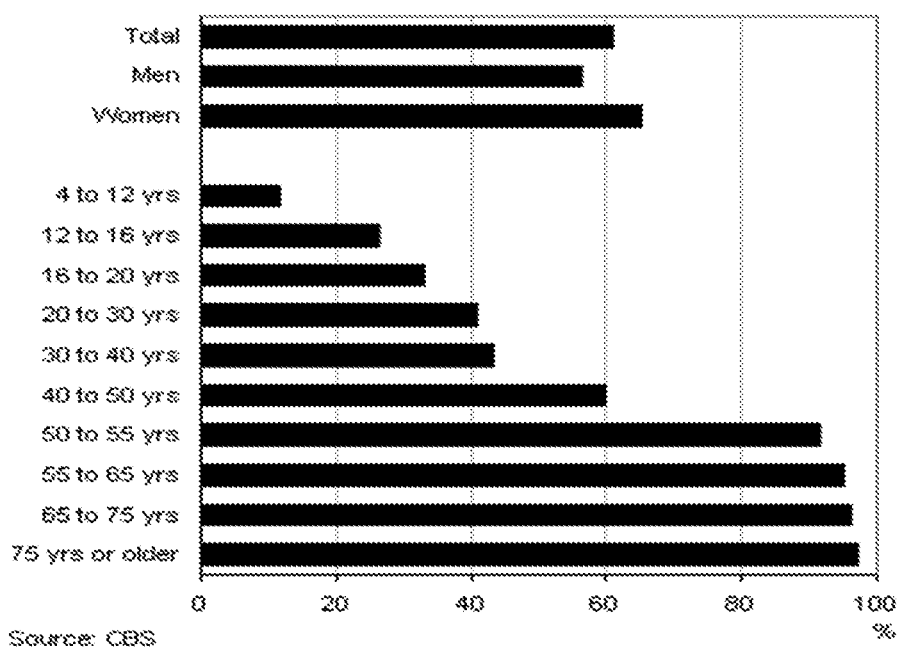
FIG. 5 shows a histogram representing the percentages of people in the world who wear prescription glasses, divided by age, based on a 2012 study, published by Cbs.nl.
Figure 6:
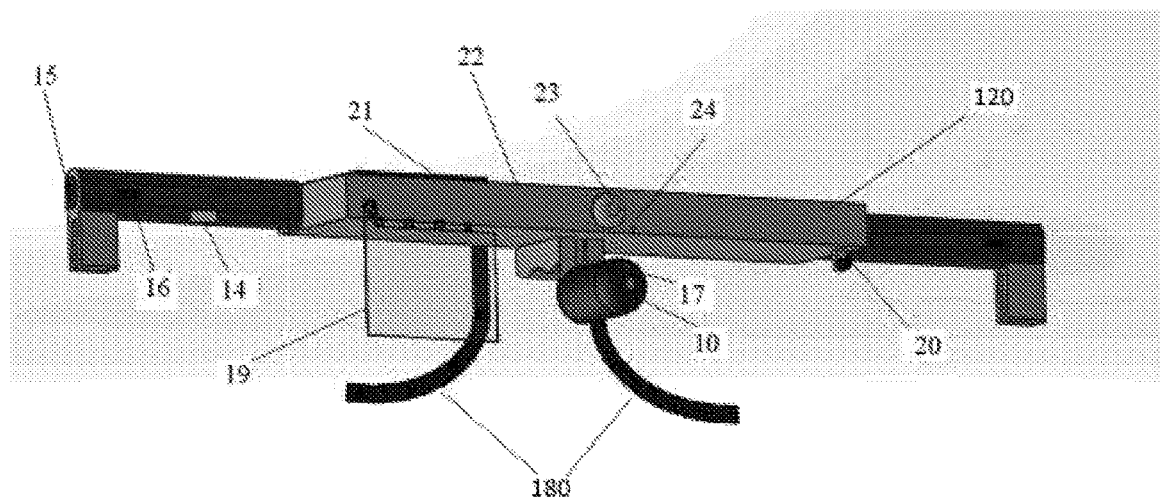
FIG. 6 shows a perspective view of a preferred embodiment of the over-glasses apparatus according to the invention.
Figure 7:
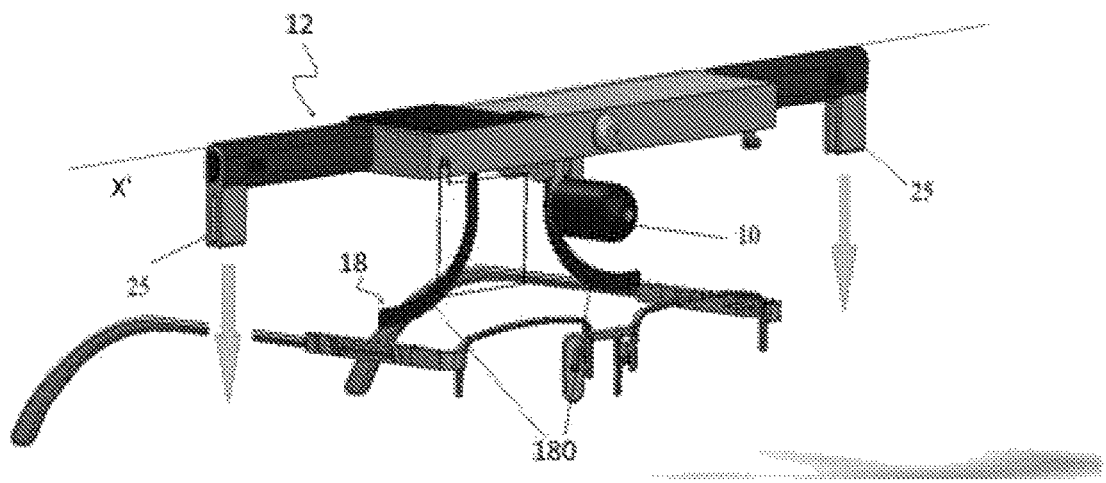
FIG. 7 shows the over-glasses apparatus of FIG. 6 while it is to coupled to a pair of glasses with the rods in the rest position.
Figure 8:
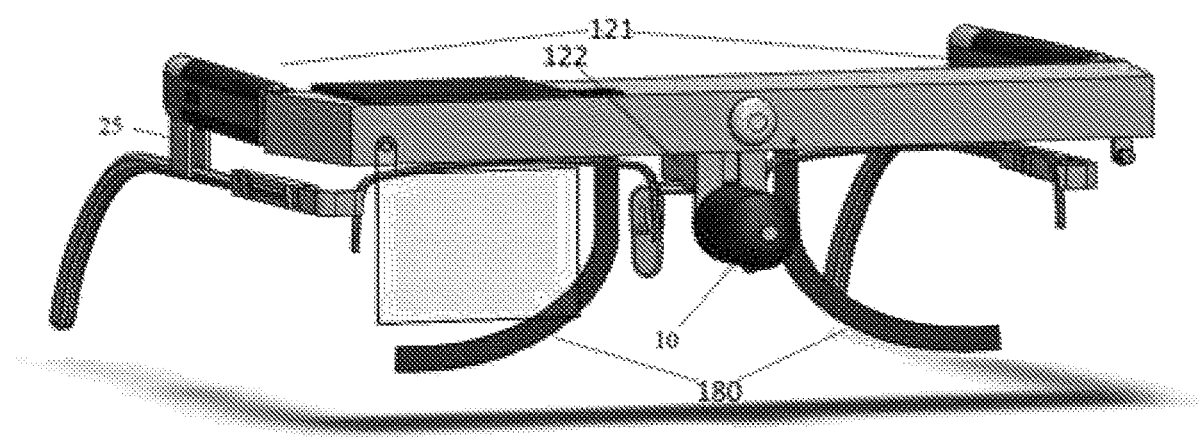
FIG. 8 shows the over-glasses apparatus of FIG. 6 coupled to a pair of glasses with the rods in the tensioned position.

Preferably, referring again to FIGS. 6-8, the support structure 12 further comprises two rods 121: each rod 121 is hinged to a respective terminal end of the main body 120, and is configured to be free to rotate from a rest position, in which it is directed substantially parallel to the direction of the main body, to a tensioned position in which it is directed substantially in an arrangement perpendicular to the main body. Each rod 121 also comprises respective coupling means 25 configured to connect each rod 121 in a removable way to a respective temple of the user's glasses. Advantageously, the support structure 12 also comprises hinge elastic means configured to exert a return rotation moment on the rods to bring them from the tensioned position to the rest position, in this way the rotation moment exerted on each rod, when connected to the rods of the glasses, allows the support structure to be firmly attached to the glasses. Referring to FIG. 5, it is particularly advantageous that the over-glasses apparatus according to the present disclosure is easily adapted to various types of glasses considering the number of people who use eyeglasses.

In one embodiment, the support structure also comprises a nosepiece support 122 configured to position itself on the bridge of the user's glasses in order to give further stability to the over-spectacle and eyewear apparatus assembly.

In one embodiment, the eye tracking system 18 comprises at least one curved elongated support 180 rigidly anchored, via a first end thereof, below the main body 120 of the support structure 12. Furthermore, the curved elongated support 180 comprises, at a second free end opposite the first end, at least one IR light source and at least one IR sensor for capturing sequential images of the eyeball. The elongated curved support 180 is configured to penetrate between the eyeglass lens and the user's eye. The eye tracking system 18 comprises preferably two elongated curved supports 180, one for each eye of the user of the over-glasses apparatus.

It should be understood that other technical embodiments of the eye tracking system 18 are possible, for example systems that include a camera placed inside the glasses at the joint between the temples and the frame.

According to variants of construction, the over-glasses apparatus also comprises:
- a miniTouchPad 21, or tactile interface device, configured to allow the user to move a monitor pointer 19 by sliding the user's finger on this miniTouchPad 21;

a sensor for the gestural commands 20 configured to scroll pages displayed on said monitor 19 and other commands with easy hand gestures;

a laser pointer 17, at the first end of shaft 3, which moves parallel to the image sensor 2, to allow confirmation of the correct observation of the environment or object observed;

a switch 14 for the laser pointer 17;

a microphone 24;

an audio reproduction device 16; and a front led light 23.

In one embodiment, referring to FIG. 4, the semi-transparent monitor 19, the microphone 24, the audio playback device 16, the image sensor 2, the eye tracking system 18, the accelerometer, the gyroscope 22, the laser pointer 17, the front LED light 23, the miniTouchPad 21 and the gesture control sensor 20 are configured to connect via cable, for example via a USB port 15, or wirelessly, for example via a Bluetooth system, to a "smart" type mobile device on which a processing and control application for the various devices is executed. Alternatively, the mobile device can only act as an interface for an application running on a remote server connected in turn with a remote-control station.

According to an alternative aspect to the previous one, the aforementioned devices are managed directly by processing and control means internal to the over-glasses apparatus.

According to another aspect, the over-glasses device does not include an internal battery and is powered via the USB port 15.

In one embodiment, the over-glasses apparatus is configured to couple to a helmet of a technical type.

The present invention has been described up to now with reference to preferred embodiments. It is to be understood that there may be other embodiments that refer to the same inventive core, as defined by the scope of the claims set out below.

The invention claimed is:

1. An over-glasses apparatus, suitable for being associated with a pair of glasses wearable by a user, said over-glasses apparatus comprising:

a support structure having a main body having a longitudinal direction of prevailing development, said support structure being configured to be positioned, when the over-glasses apparatus is associated with the worn glasses, above the lenses according to an arrangement in which said longitudinal direction of prevailing development is substantially parallel to an inter-pupillary axis (X);

an eye tracking system, suitable for detecting the movement of a user's pupils;

an image sensor configured to be at a same level as the user's pupils when the over-glasses apparatus is associated with the worn glasses;

an actuation system of said image sensor, suitable for allowing a rotation of said image sensor at least around a first axis (X) and a second axis (Y) of a Cartesian axis system (X, Y, Z), in which, in use, said first axis (X) is an interpupillary axis substantially joining the user's pupils and said second axis (Y) is substantially lying in the sagittal plane; and processing and control means, programmed to receive in input a detection signal provided by said eye tracking system and to control said actuation system as a function of said detection signal according to respective angles of rotation of said image sensor around said first (X) and second (Y) axis, so that said image sensor is continuously oriented according to the user's gaze;

wherein said image sensor and actuation system are comprised inside a camera housing arranged substantially in correspondence with a longitudinally median portion of said main body, so that said camera housing intercepts said first axis (X), and said image sensor is disposed on a first end of a shaft and a body is disposed on a second end of said shaft opposite said first end, a structural constraint supports said shaft at an intermediate point between said first end and said second end substantially at an origin of said first axis (X) and said second axis (Y), and said actuation system is configured to generate a force on said body to rotate said first end of said shaft with said image sensor about said first axis (X) and said second axis (Y).

2. The over-glasses apparatus according to claim 1 comprising means for adjusting the position of said camera housing on the main body with respect to the second axis (Y).

3. The over-glasses apparatus according to claim 1, further comprising a linear actuator configured to move the camera housing linearly according to the third axis (Z).

4. The over-glasses apparatus according to claim 1, wherein the support structure comprises two rods, each rod being hinged to a respective terminal end of the main body and being configured to rotate from a rest position, in which it is directed substantially according to an arrangement parallel to said longitudinal direction of development of the main body, to a tensioned position in which each said rod is substantially directed according to an arrangement perpendicular to the main body, and further comprising respective coupling means configured to connect each rod in a removable way to a respective temple of the glasses of the user, the support structure further comprising hinge elastic means configured to exert a return rotation moment on the rods to bring them from the tensioned position to the rest position, in this way the moment of rotation exerted on the rods when they are connected to the temples of the glasses allows the support structure to be firmly attached to the glasses.

5. The over-glasses apparatus according to claim 1, in which the camera housing comprises an optical group configured to be placed in front of the image sensor.

6. The over-glasses apparatus according to claim 1, wherein the eye tracking system comprises at least one elongated curved support rigidly anchored, through a first end thereof, below the main body of the support structure and configured to penetrate between the eyeglass lens and the user's eye, said curved support comprising at a second free end opposite the first end, at least one IR light source and at least one IR sensor to capture sequential images of the eyeball.

7. The over-glasses apparatus according to claim 1, further comprising a USB port configured to electrically power said over-glasses apparatus.

8. The over-glasses apparatus according to claim 6, further comprising a semi-transparent monitor configured to be positioned in front of one of the lenses of the glasses and to display information visible in transparency to the user of the over-glasses apparatus.

9. The over-glasses apparatus according to claim 8, wherein said camera housing further comprises a laser pointer having a direction substantially parallel to a longitudinal development direction of said shaft.

10. The over-glasses apparatus according to claim 9, which further comprises:
- an accelerometer;
- a gyroscope;
- a miniTouchPad configured to allow the user to move a monitor pointer by sliding the user's finger on said miniTouchPad;
- a sensor for gesture commands configured to scroll pages displayed on said monitor;
- a microphone;
- an audio reproduction device; and
- a front led light.

11. The over-glasses apparatus according to claim 10, wherein the semi-transparent monitor, the microphone, the audio reproduction device, the image sensor, the eye tracking system, the accelerometer and gyroscope, the laser pointer, the front LED light, the miniTouchPad and the sensor for gesture commands are configured to connect, via cable or wirelessly, to a mobile device running a processing and control application of the various devices.

12. The over-glasses apparatus according to claim 1, wherein said body includes ferromagnetic material and said actuation system includes inductors arranged and configured to generate magnetic forces on the body to rotate said first end of said shaft about said first axis and said second axis.

13. The over-glasses apparatus according to claim 1, wherein the structural constraint prevents transverse movement of the intermediate point of the shaft.

14. An over-glasses apparatus suitable for being attached to a pair of glasses wearable by a user, said over-glasses apparatus comprising:
- a support structure having a main body having a longitudinal direction of prevailing development, said support structure being configured to be positioned, when the over-glasses apparatus is attached to the worn glasses, above the lenses according to an arrangement in which said longitudinal direction of prevailing development is substantially parallel to an inter-pupillary axis;
- an eye tracking system, suitable for detecting the movement of at least one of the user's pupils;
- an image sensor configured to be at a same level as the user's pupils when the over-glasses apparatus is associated with the worn glasses;
- an actuation system of said image sensor, suitable for allowing a rotation of said image sensor at least around a first axis and a second axis of a Cartesian axis system, in which, in use, said first axis is an interpupillary axis substantially joining the user's pupils and said second axis is substantially lying in the sagittal plane; and
- processing and control means, programmed to receive in input a detection signal provided by said eye tracking system and to control said actuation system as a function of said detection signal according to respective angles of rotation of said image sensor around said first axis and second axis, so that said image sensor is continuously oriented according to the user's gaze;
- wherein said image sensor and actuation system are comprised inside a camera housing arranged substantially in correspondence with a longitudinally median portion of said main body, so that said camera housing intercepts said first axis,
- and wherein said actuation system of said image sensor comprises a shaft, said image sensor being connected at a first end of said shaft, a body in ferromagnetic material being connected at a second end, opposite to the first, of said shaft, wherein said shaft is constrained to said camera housing, with respect to translation movement, at an intermediate point between the first and the second end of said shaft by means of a structural constraint, said structural constraint being configured to allow the rotation of the shaft, initially directed along a third axis of said Cartesian axis system, around said first axis and said second axis and wherein said actuation system of said image sensor further comprises at least four inductors, rigidly connected to, and inside, said camera housing, arranged along a circumferential path at regular intervals in a plane parallel to a plane defined by the first axis and second axis of the Cartesian axis system, said body being substantially in correspondence of the centre of said circumferential path when the shaft is directed according to the third axis, these inductors being configured to be controlled by a control signal output by said processing and control means so that the electromagnetic fields generated have an attraction or repulsion effect on the body with a consequent rotational movement around the first axis and the second axis of the image sensor.

15. The over-glasses apparatus according to claim 14, wherein the rotation of the shaft around the first axis and the second axis is between an interval of ±80° and ±60° with respect to the initial position of the shaft directed according to the third axis.

16. The over-glasses apparatus according to claim 14, wherein said actuation system of said image sensor comprises springback means, a first end of which is connected to the body and a second end of which, opposite to the first, is connected to the camera housing, said springback means are configured to be in a rest position when the shaft is directed according to the third axis and to exert an elastic return force when the body is attracted by one or more of the inductors, this elastic return force being able to bring said shaft back in the direction of the third axis.

* * * * *